US009511194B2

(12) United States Patent
Hourmand et al.

(10) Patent No.: US 9,511,194 B2
(45) Date of Patent: *Dec. 6, 2016

(54) AUTOINJECTOR (71) Applicant: SANOFI-AVENTIS DEUTSCHLAND GMBH, Frankfurt am Main (DE)

(72) Inventors: Yannick Hourmand, Cambridgeshire (GB); Simon Brereton, Cambridgeshire (GB); Thomas Mark Kemp, London (GB); Rosie Burnell, Cambridgeshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 185 days.

This patent is subject to a terminal disclaimer.

(21) Appl. No.: 14/364,242

(22) PCT Filed: Dec. 19, 2012

(86) PCT No.: PCT/EP2012/076098
§ 371 (c)(1),
(2) Date: Jun. 10, 2014

(87) PCT Pub. No.: WO2013/092671
PCT Pub. Date: Jun. 27, 2013

(65) Prior Publication Data
US 2014/0336590 A1    Nov. 13, 2014

(30) Foreign Application Priority Data
Dec. 21, 2011   (EP) .................................. 11194778

(51) Int. Cl.
*A61M 5/32*      (2006.01)
*A61M 5/20*      (2006.01)
*A61M 5/315*     (2006.01)

(52) U.S. Cl.
CPC ......... *A61M 5/3204* (2013.01); *A61M 5/2033* (2013.01); *A61M 5/31511* (2013.01); *A61M 5/326* (2013.01); *A61M 2005/206* (2013.01)

(58) Field of Classification Search
CPC .............. A61M 2005/2026; A61M 2005/206; A61M 5/2033; A61M 2005/2073; A61M 5/20; A61M 2005/202; A61M 2005/2013
See application file for complete search history.

(56) References Cited

U.S. PATENT DOCUMENTS 8,876,768 B2 * 11/2014 Hourmand .......... A61M 5/2033
                                                            604/134
2007/0135767 A1 *  6/2007 Gillespie, III ...... A61M 5/2033
                                                            604/135

(Continued)

FOREIGN PATENT DOCUMENTS

DE      102007013836      9/2008
EP         2399630        12/2011

(Continued)

OTHER PUBLICATIONS

International Search Report for Int. App. No. PCT/EP2012/076098, completed Apr. 2, 2013.

Primary Examiner — Kevin C. Sirmons
Assistant Examiner — William Carpenter
(74) Attorney, Agent, or Firm — Fish & Richardson P.C.

(57) ABSTRACT

Described is an autoinjector comprising a case, a needle shroud slidably arranged in the case, a chassis slidably arranged in the case and rotatably coupled to the needle shroud, an outer plunger selectively engaged to the chassis, an inner plunger selectively engaged to the outer plunger, and a drive spring applying a biasing force to the outer plunger. The biasing force is applied to the inner plunger when the inner plunger is engaged to the outer plunger. Axial movement of the needle shroud relative to the case causes rotation of the chassis relative to the needle shroud. The rotation of the chassis causes the inner plunger to rotate relative to the outer plunger and disengage the outer plunger to remove the biasing force from the drive spring on the inner plunger.

15 Claims, 11 Drawing Sheets

(56) References Cited

U.S. PATENT DOCUMENTS

| | | | | |
|---|---|---|---|---|
| 2011/0313364 A1* | 12/2011 | Rolfe | ............... | A61M 5/2033 604/198 |
| 2013/0079718 A1* | 3/2013 | Shang | ............... | A61M 5/20 604/131 |
| 2013/0123710 A1* | 5/2013 | Ekman | ............... | A61M 5/2033 604/198 |
| 2013/0131595 A1* | 5/2013 | Ekman | ............... | A61M 5/1452 604/117 |
| 2013/0131602 A1* | 5/2013 | Kemp | ............... | A61M 5/2033 604/197 |
| 2013/0150801 A1* | 6/2013 | Ekman | ............... | A61M 5/2033 604/198 |
| 2013/0267898 A1* | 10/2013 | Hourmand | ............... | A61M 5/2033 604/135 |
| 2013/0274676 A1* | 10/2013 | Ekman | ............... | A61M 5/2033 604/197 |
| 2014/0343508 A1* | 11/2014 | Hourmand | ............... | A61M 5/2033 604/198 |

FOREIGN PATENT DOCUMENTS

| EP | 2438947 | 4/2012 |
|---|---|---|
| WO | 2011/101383 | 8/2011 |

* cited by examiner

AUTOINJECTOR

CROSS REFERENCE TO RELATED APPLICATIONS

The present application is a U.S. National Phase Application pursuant to 35 U.S.C. §371 of International Application No. PCT/EP2012/076098 filed Dec. 19, 2012, which claims priority to European Patent Application No. 11194778.4 filed Dec. 21, 2011. The entire disclosure contents of these applications are herewith incorporated by reference into the present application.

TECHNICAL FIELD

The invention relates to an autoinjector for administering a medicament.

BACKGROUND

Administering an injection is a process which presents a number of risks and challenges for users and healthcare professionals, both mental and physicalInjection devices typically fall into two categories—manual devices and auto-injectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to present invention comprises a case, a needle shroud slidably arranged in the case, a chassis slidably arranged in the case and rotatably coupled to the needle shroud, an outer plunger selectively engaged to the chassis, an inner plunger selectively engaged to the outer plunger, and a drive spring applying a biasing force to the outer plunger. The biasing force is applied to the inner plunger when the inner plunger is engaged to the outer plunger. Axial movement of the needle shroud relative to the case causes rotation of the chassis relative to the needle shroud. The rotation of the chassis causes the inner plunger to rotate relative to the outer plunger and disengage the outer plunger to remove the biasing force from the drive spring on the inner plunger.

In an exemplary embodiment, the autoinjector further comprises a firing nut rotatably disposed on the chassis. The firing nut engages the outer plunger when in a first angular position and disengaging the outer plunger when in a second angular position.

In an exemplary embodiment, the autoinjector further comprises a trigger button coupled to the case and selectively engaging the firing nut. Axial movement of the trigger button relative to the case causes rotation of the firing nut from the first angular position to the second angular position. When the firing nut is in the second angular position, the biasing force of the drive spring pushes the outer plunger in a distal direction relative to the case and pushes the chassis in a proximal direction relative to the case.

In an exemplary embodiment, the needle shroud has a first axial position in which a first portion of the needle shroud extends beyond a distal end of the case, a second axial position in which the needle shroud is retracted into the case, and a third axial position in which a second portion of the needle shroud longer than the first portion extends beyond the distal end of the case. In the first axial position, resilient shroud latches on the needle shroud abut shoulders on the case. The outer plunger engages the shroud latches which deflect and do not engage the shoulders on the case when the needle shroud translates from the second axial position to the third axial position.

In an exemplary embodiment, the needle shroud includes a guide track adapted to engage a pin on the chassis. The pin moves from an angled portion to an axial portion of the guide track causing rotation of the chassis relative to the needle shroud when the needle shroud translates from the second axial position to the third axial position.

In an exemplary embodiment, the autoinjector further comprises a syringe carrier slidably disposed in the case. The syringe carrier is adapted to hold a syringe.

In an exemplary embodiment, the autoinjector further comprises a coupling carrier coupled to the syringe carrier and selectively engaged to the inner plunger. The coupling carrier includes resilient arms adapted to releasably engage the inner plunger, and the biasing force of the drive spring causes the inner plunger to deflect the resilient arms when a front stop on the syringe carrier abuts a shroud shoulder on the needle shroud. When the resilient arms disengage the inner plunger, the inner plunger is adapted to push a stopper in the syringe. The chassis includes a resilient clip adapted to engage a stop on the coupling carrier when the needle shroud is in the third axial position.

In an exemplary embodiment, the autoinjector further comprises a control spring axially biasing the needle shroud relative to the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
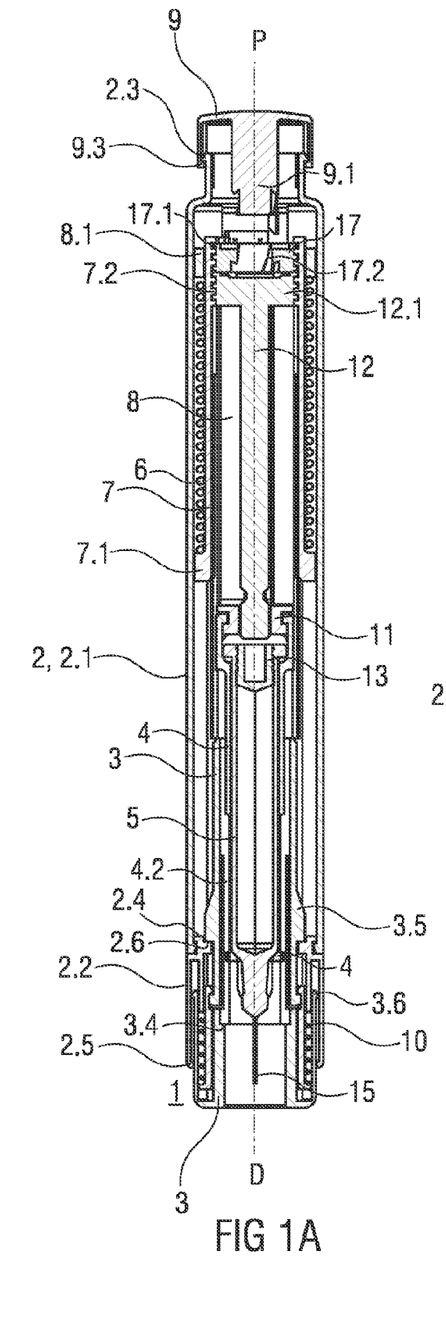
FIGS. 1A and 1B show two longitudinal sections of an exemplary embodiment of an autoinjector in an initial state according to the present invention.
Figure 1B:
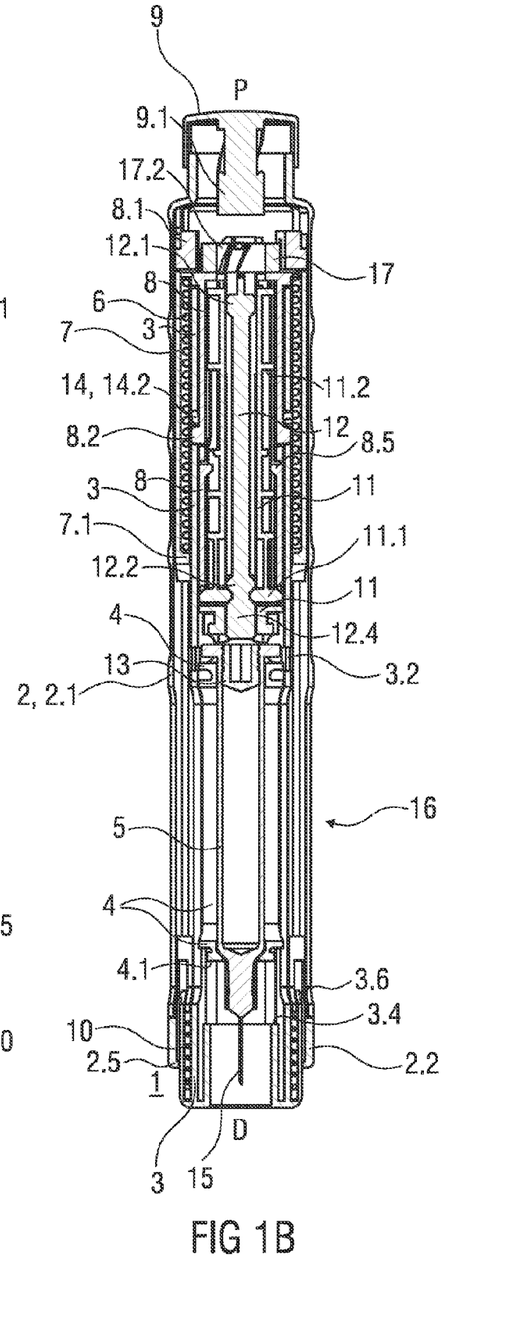
Figure 2:
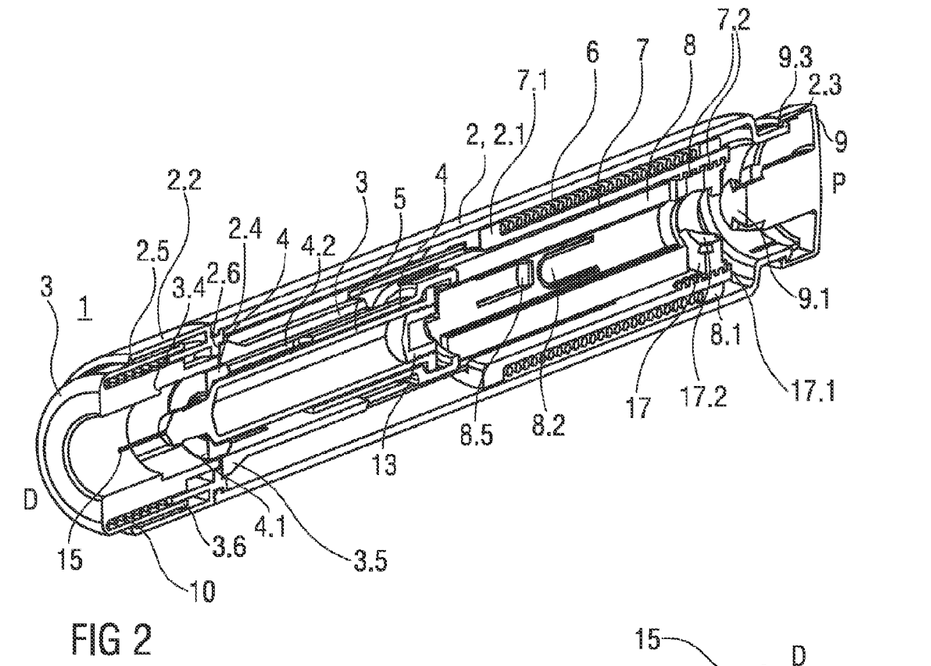
FIG. 2 is a perspective longitudinal section of an exemplary embodiment of an autoinjector in an initial state according to the present invention.

FIGS. 1A and 1B show two longitudinal sections of an exemplary embodiment of an autoinjector 1 for delivering a medicament. The sectional planes of the longitudinal sections are essentially oriented perpendicularly with respect to each other. FIG. 2 shows a respective perspective sectional view of an exemplary embodiment of the autoinjector 1.

In an exemplary embodiment, the autoinjector 1 comprises an elongate case 2 comprising a rear case 2.1 coupled to a front case 2.2. A needle shroud 3 is telescopically arranged on the case 2 and may be resiliently coupled to the front case 2.2 by a control spring 10 which applies a biasing force on the needle shroud toward a distal direction D. In an exemplary embodiment, the control spring 10 may be preloaded. Resilient latch arms 3.5 on the needle shroud 3 are adapted to engage a shoulder 2.6 on the front case 2.2 to limit axial movement of the needle shroud 3 relative to the case 2 in the distal direction D.

A syringe carrier 4 is slidably disposed in the case 2 and is arranged to hold a syringe 5 having a needle 15. As explained further below, the syringe carrier 4 includes an abutment surface 4.1 formed on its distal end and is adapted to abut a shoulder 3.4 formed on the distal portion of the needle shroud 3 when the syringe carrier 4 is moving axially in the distal direction D relative to the needle shroud 3. A distance between a distal face of the needle shroud 3 and the shoulder 3.4 may define the injection depth of the needle 15.

As shown in FIG. 2, prior to an injection, the syringe carrier 4 abuts the latch arms 3.5 on the needle shroud 3 and prevents the latch arms 3.5 from deflecting radially and disengaging the case 2. As explained further below, the syringe carrier 4 includes lateral apertures 4.2 which, when aligned with the latch arms 3.5 provide space for allowing the latch arms 3.5 to deflect radially and disengage the case 2.

Referring back to FIGS. 1A and 1B, a proximal end of the needle shroud 3 is adapted to abut a chassis 8 which slidably disposed in the case 2. A collar 8.1 disposed on a proximal end of the chassis 8 acts as a proximal bearing for a drive spring 6, which bears distally on a shoulder 7.1 on an outer plunger 7 that is telescopically arranged on the chassis 8.

Figure 9:
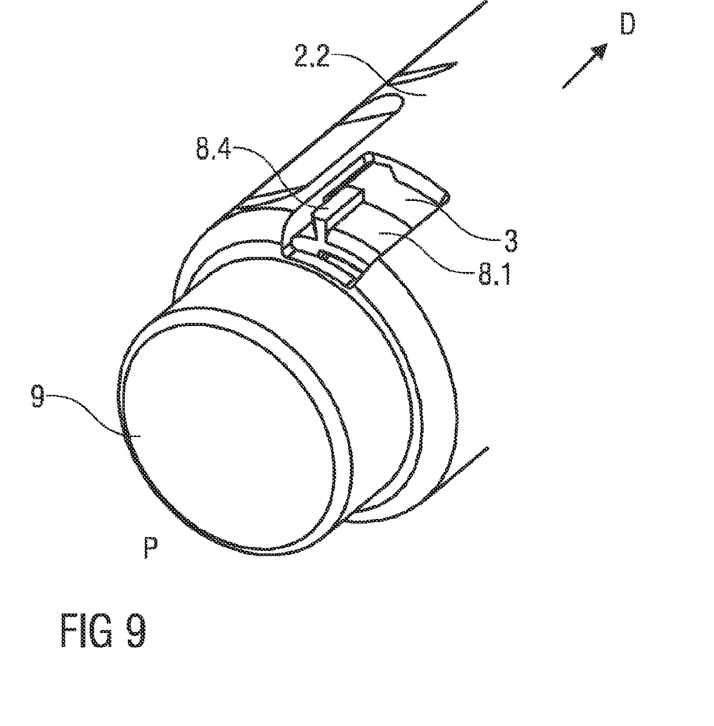
FIG. 9 is a perspective view of a proximal end of an exemplary embodiment of an autoinjector during an injection according to the present invention.
Figure 12:
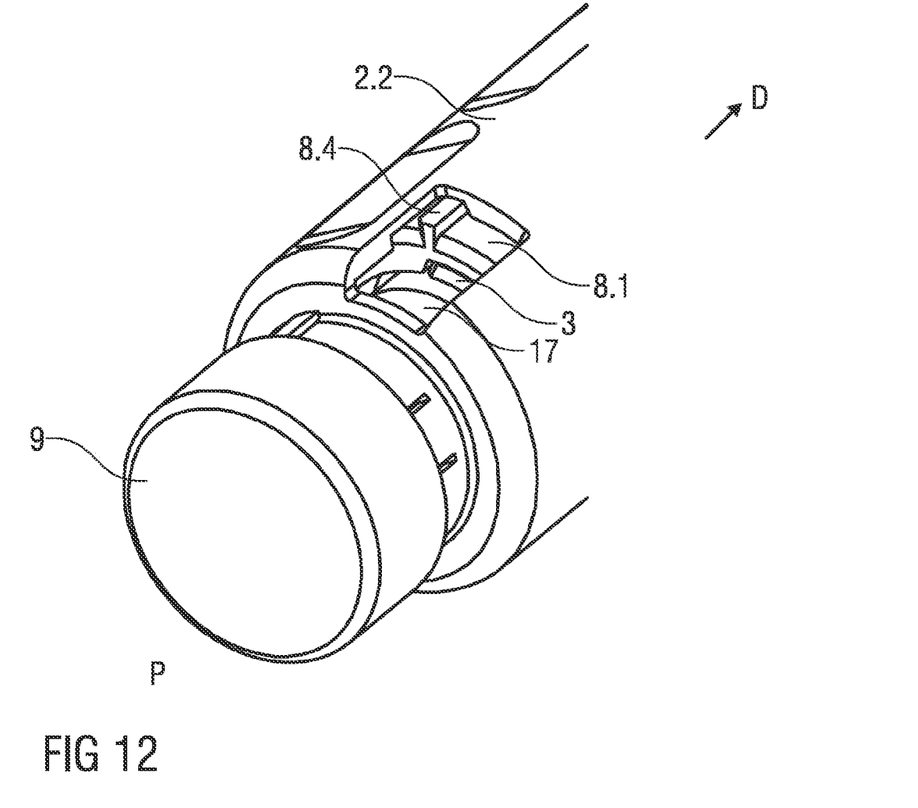
FIG. 12 is a perspective view of a proximal end of an exemplary embodiment of an autoinjector before and after an injection according to the present invention.

As shown in FIG. 12, in an exemplary embodiment, the collar 8.1 includes a radial protrusion 8.4 which is adapted to prevent rotation of the chassis 8 relative to the rear case 2.1 when the autoinjector 1 is pressed against an injection site. In an exemplary embodiment, the radial protrusion 8.4 is adapted to engage a channel formed in the rear case 2.1, and when the needle shroud 3 is pressed against the injection site, the radial protrusion 8.4 abuts the channel and is prevented from rotating relative to the rear case 2.1, as shown in FIG. 9. Prior to and after use, the radial protrusion 8.4 does not abut the channel and thus the collar 8.1 (and chassis 8) may rotate relative to the rear case 2.1.

In an exemplary embodiment, a firing nut 17 is selectively engaged to outer plunger 7. The firing nut 17 may rotatably sit in a cavity of the collar 8.1. The firing nut 17 may include teeth 17.1 which are adapted to engage teeth 7.2 formed on a surface of the outer plunger 7. The teeth 17.1 on the firing nut 17 may be formed on a selected portion of the firing nut 17, such that rotation of the firing nut 17 relative to the outer plunger 7 from a first angular position to a second angular position may disengage the outer plunger from the firing nut 17.

Figure 3:
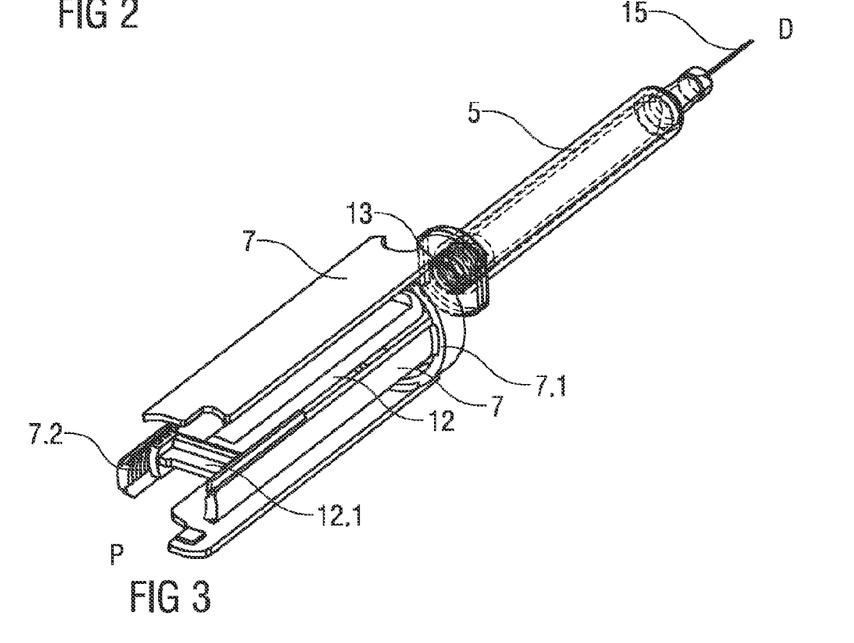
FIG. 3 is a perspective view of exemplary embodiments of a syringe, an inner plunger and an outer plunger for an autoinjector according to the present invention.

As shown in FIG. 3, the teeth 7.2 of the outer plunger 7 may also engage corresponding teeth 12.1 formed on an inner plunger 12. For example, the inner plunger 12 may include a stem and a transverse element coupled to a proximal portion of the stem, and an outer surface of the transverse element may include the teeth 12.1 for engaging the teeth 7.2 on the outer plunger 7.

Figure 4:
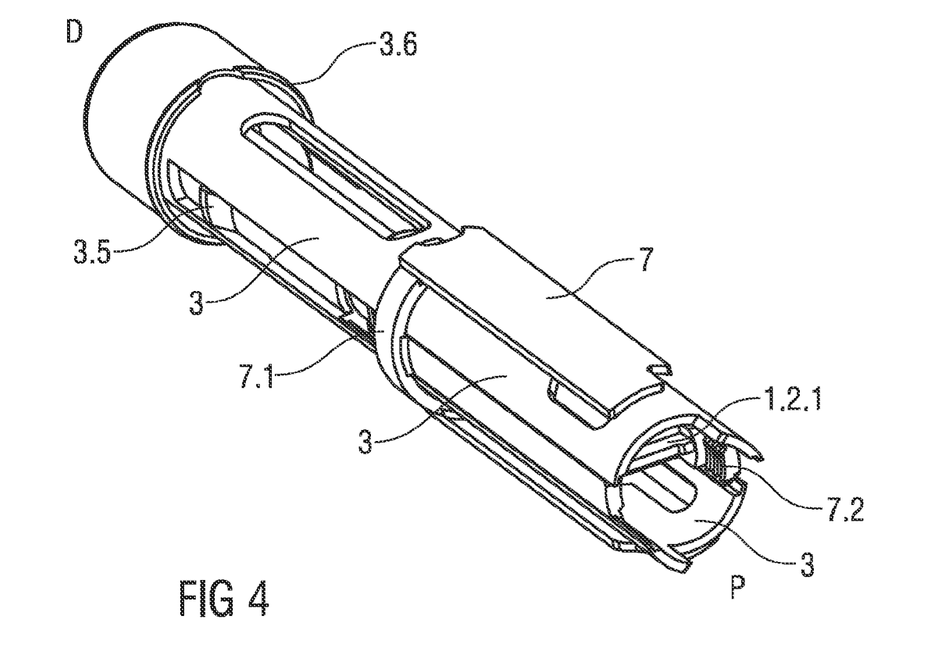
FIG. 4 is a perspective view of an exemplary embodiment of an outer plunger guided in a needle shroud according to the present invention.

As shown in FIG. 4, the outer plunger 7 may be keyed to the needle shroud 3 to allow axial relative movement but prevent rotational relative movement. For example, the outer plunger 7 may include a plurality of legs, and one or more of the legs may be adapted to engage a groove or channel formed in the needle shroud 3.

Referring back to FIGS. 1A and 1B, a coupling carrier 11 is slidably arranged in and keyed to the chassis 8 (allowing for relative translation and joint rotation) and is coupled to the syringe carrier 4. The inner plunger 12 is arranged telescopically in the coupling carrier 11 to allow for axial movement of the inner plunger 12 relative to the coupling carrier 11 and joint rotation with the coupling carrier 11 relative to the chassis 8. Two resilient arms 11.1 on the coupling carrier 11 are arranged to selectively engage a groove between a first plunger shoulder 12.2 and a second plunger shoulder 12.4 on the inner plunger 12 in a manner to couple the inner plunger 12 and the coupling carrier 11 for joint axial translation. In an exemplary embodiment, the resilient arms 11.1 and the first plunger shoulder 12.2 are in a ramped engagement so as to allow the resilient arms 11.1 to deflect radially and disengage the inner plunger 12.

In an exemplary embodiment, the resilient arms 11.1 are maintained in engagement with the first plunger shoulder 12.2, because the needle shroud 3 abuts the resilient arms 11.1. However, the needle shroud 3 includes first apertures 3.2 which, when aligned with the resilient arms 11.1, allow space for the resilient arms 11.1 to deflect radially and disengage the inner plunger 12.

In an exemplary embodiment, a trigger button 9 is arranged on the autoinjector 1 to allow triggering an injection. In an exemplary embodiment, the trigger button 9 is arranged on a proximal end of the autoinjector 1 and positioned for thumb activation. However, those of skill in the art will understand that the trigger button 9 may be disposed on a side of the case 2 or the autoinjector 1 may not include a trigger button 9, but be activated when pressed against an injection site. In an exemplary embodiment, the trigger button 9 is resiliently biased in the proximal direction P by a button spring (not shown) which is distally grounded on, for example, the chassis 8 or the firing nut 17 and proximally grounded on an inner surface of the trigger button 9. The trigger button 9 may remain coupled to the case 2 by the engagement of hooks 9.3 on the trigger button 9 and hooks 2.3 on the proximal end of the rear case 2.

In an exemplary embodiment, the trigger button 9 includes a stem 9.1 extending in the proximal direction and having a thread adapted to engage a corresponding thread 17.2 formed in the firing nut 17. As explained further below, when the thread on the stem 9.1 engages the thread 17.2 on the firing nut 17, the firing nut 17 rotates relative to the outer plunger 7.

In an exemplary embodiment, a cap (not shown) is removably coupled to the front case 2.2 and/or the needle shroud 3. The cap may be coupled to a needle sheath (not illustrated) arranged on the needle 15, and removal of the cap may remove the needle sheath.

Figure 8:
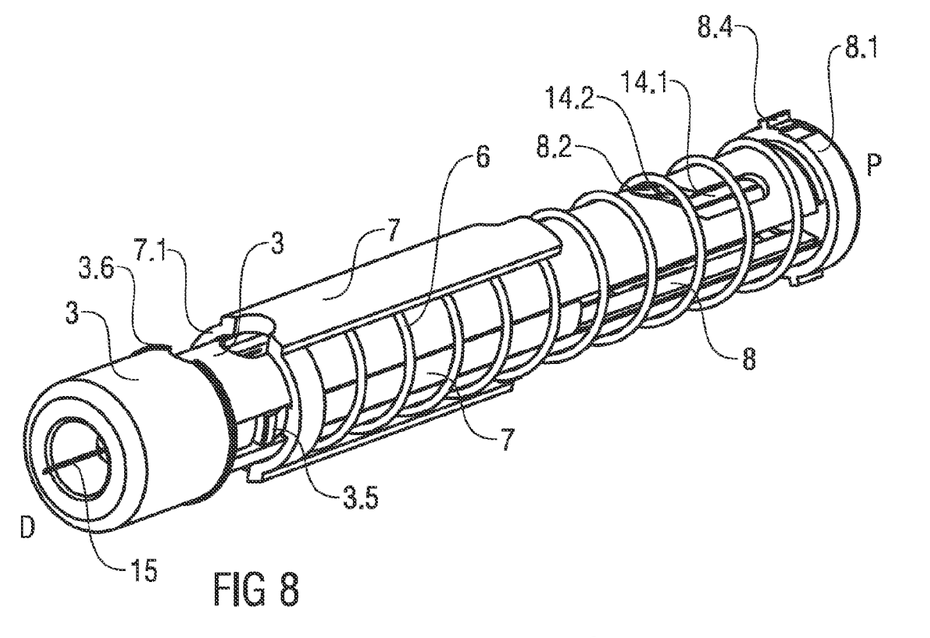
FIG. 8 is a perspective view of exemplary embodiments of internal components of an exemplary embodiment of an autoinjector with a needle extended according to the present invention.

FIGS. 1A and 1B show the autoinjector 1 in an initial state, prior to use. Prior to use, the needle shroud 3 extends from the case 2 under the biasing force of the control spring 10 to cover a distal tip of the needle 15. The extension of the needle shroud 3 relative to the case 2 is limited by the engagement of the shroud latch 3.5 and the shoulder 2.6 on the front case 2.2. As shown in FIG. 8, in an exemplary embodiment, the needle shroud 3 includes a guide track 14 having an axial portion 14.1 and an angle portion 14.2, and a pin 8.2 on the chassis 8 engages the guide track 14. In the initial state, the pin 8.2 is in a distal portion of the angled section 14.2. Referring back to FIGS. 1A and 1B, the firing nut 17 and the inner plunger 12 are both engaged to the outer plunger 7, and the coupling carrier 11 is engaged to the inner plunger 12. In the initial state, there is a sufficient distance between the stem 9.1 of the trigger button 9 and the firing nut 17, such that even if the trigger button 9 is pressed, the autoinjector 1 will not be activated when it is not pressed against an injection site.

Figure 5A:
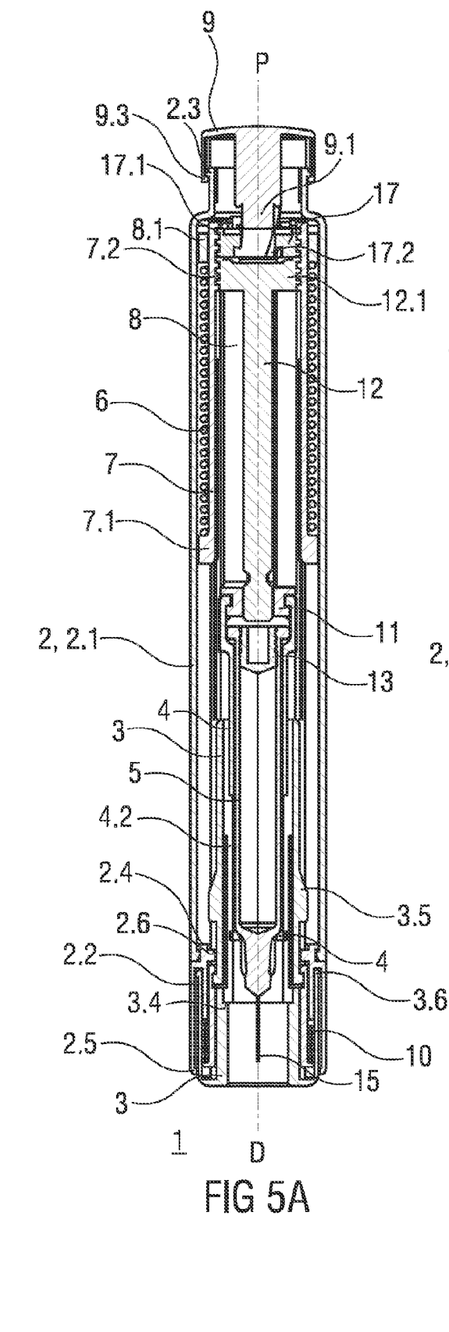
FIGS. 5A and 5B show two longitudinal sections of an exemplary embodiment of an autoinjector with a distal end pushed against an injection site according to the present invention.
Figure 5B:
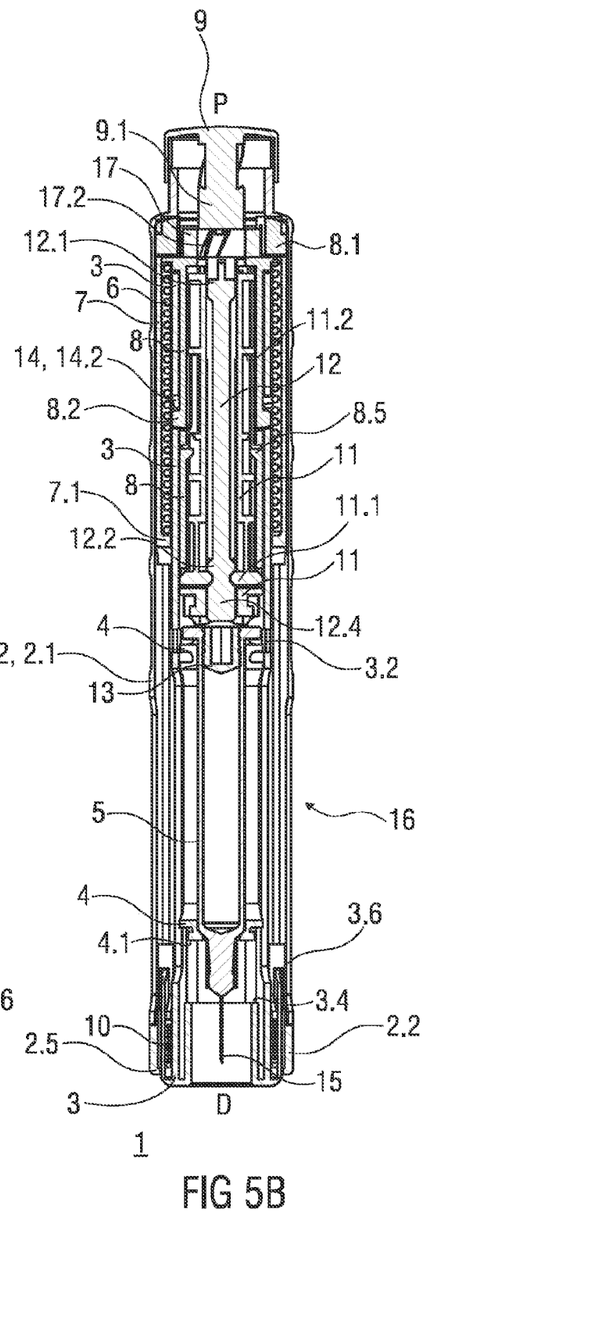

As shown in FIGS. 5A and 5B, when the autoinjector 1 is pressed against an injection site, the needle shroud 3 translates into the case 2 in the proximal direction P, compressing the control spring 10. The needle shroud 3 pushes the chassis 8 in the proximal direction P. Movement of the chassis 8 results in corresponding movement of the firing nut 17 which also results in corresponding movement of the outer plunger 7, since the firing nut 17 is engaged to the outer plunger 7 via teeth 17.1. Since the inner plunger 12 is engaged to the outer plunger 7, the inner plunger 12 and the coupling carrier 11, the syringe carrier 4 and the syringe 5 move in conjunction with the inner plunger 12.

Figure 6A:
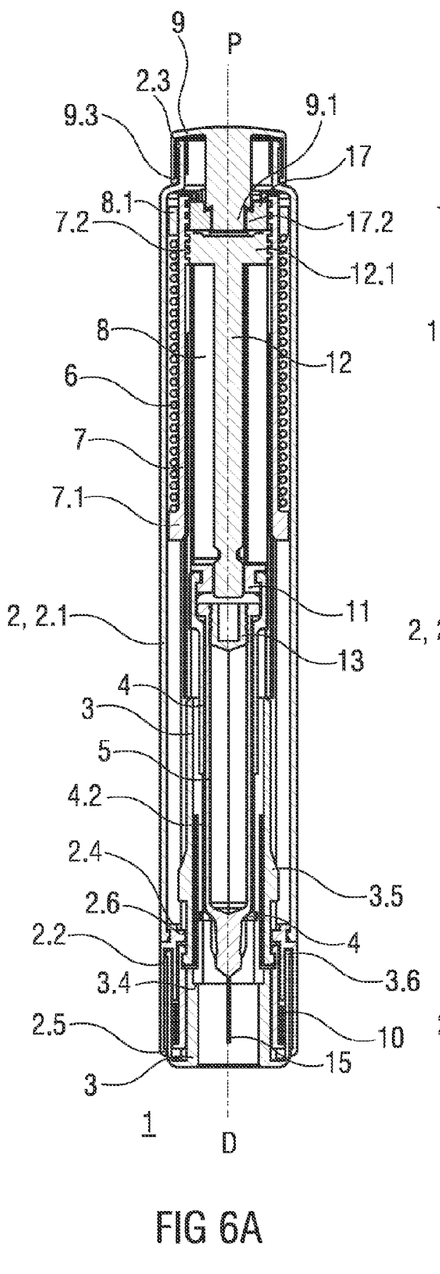
FIGS. 6A and 6B show two longitudinal sections of an exemplary embodiment of an autoinjector with a trigger button depressed according to the present invention.
Figure 6B:
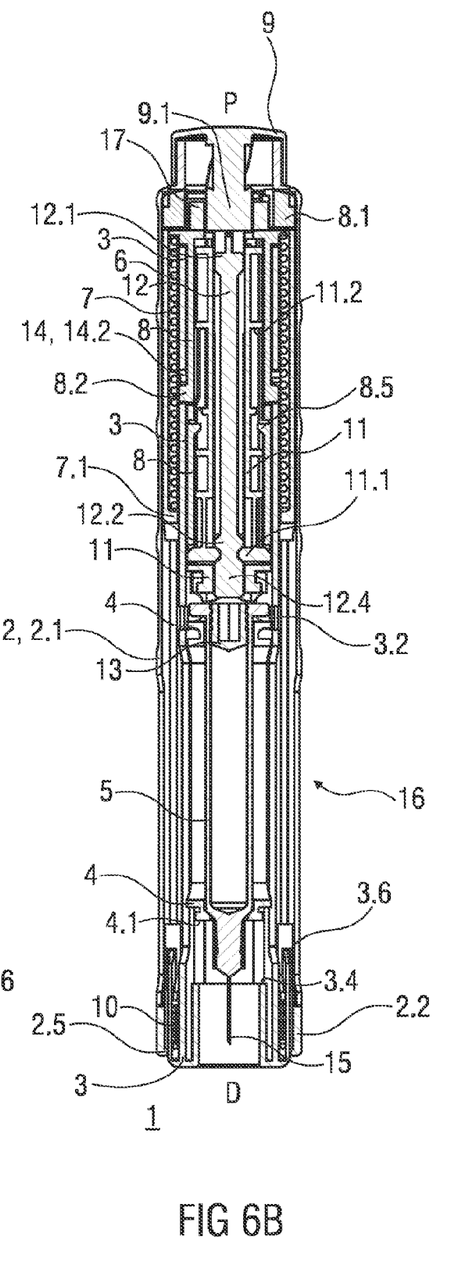

As shown in FIGS. 6A and 6B, the trigger button 9 is pressed, and the stem 9.1 engages the firing nut 17. As the stem 9.1 moves in the distal direction D and engages the firing nut 17, the firing nut 17 rotates from the first angular position to the second angular position, disengaging the outer plunger 7.

Figure 7A:
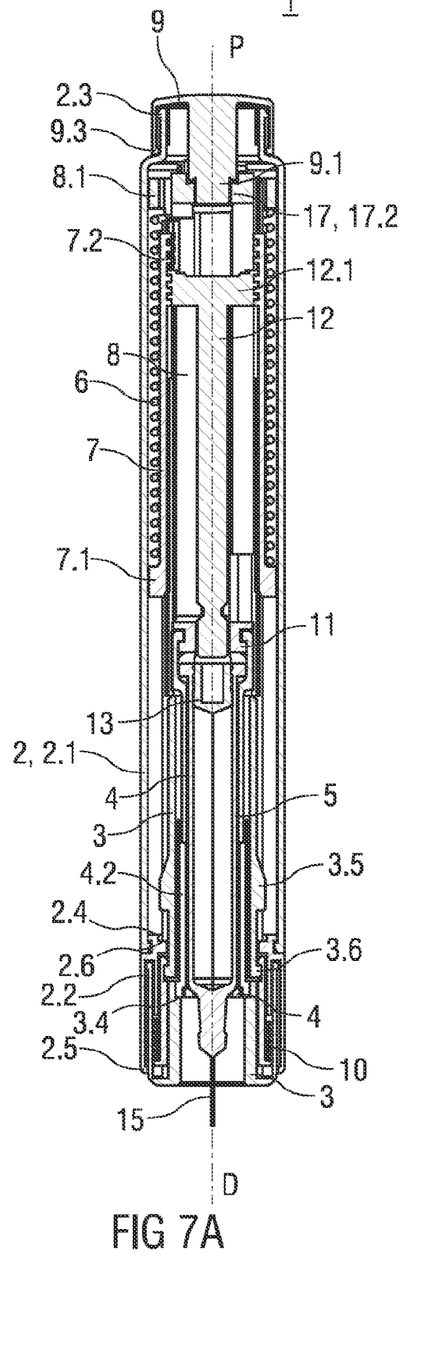
FIGS. 7A and 7B show two longitudinal sections of an exemplary embodiment of an autoinjector with an injection needle extended beyond the distal end according to the present invention.
Figure 7B:
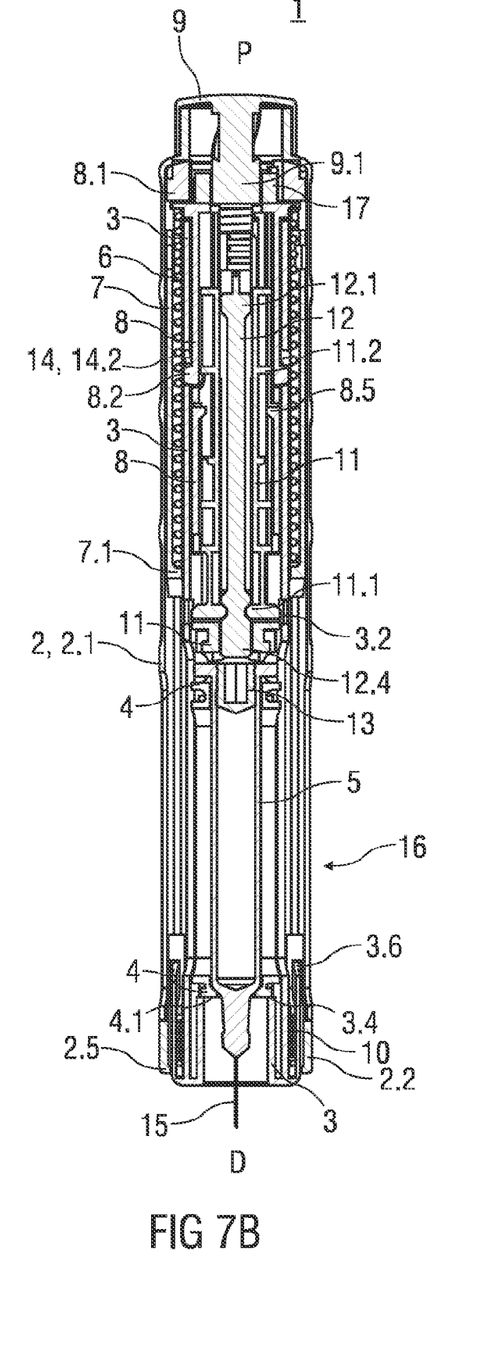

As shown in FIGS. 7A and 7B, when the firing nut 17 rotates into the second angular position, the outer plunger 7 is released, and the drive spring 6 pushes the outer plunger 7 in the distal direction D. As the inner plunger 12 is coupled to the outer plunger 7, the inner plunger 12 (and the coupling carrier 11, syringe carrier 4 and syringe 5) moves in the distal direction D. Movement of the syringe carrier 4 in the distal direction D leads to insertion of the needle 15 in the injection site. A penetration depth of the needle 15 is defined by a front stop 4.1 on the syringe carrier 4 abutting an inner distal shroud shoulder 3.4 on the needle shroud 3.

Additionally, the drive spring 6 applies a proximally directed force on the collar 8.1 to maintain it in a position abutting the proximal end of the rear case 2.1.

Figure 10A:
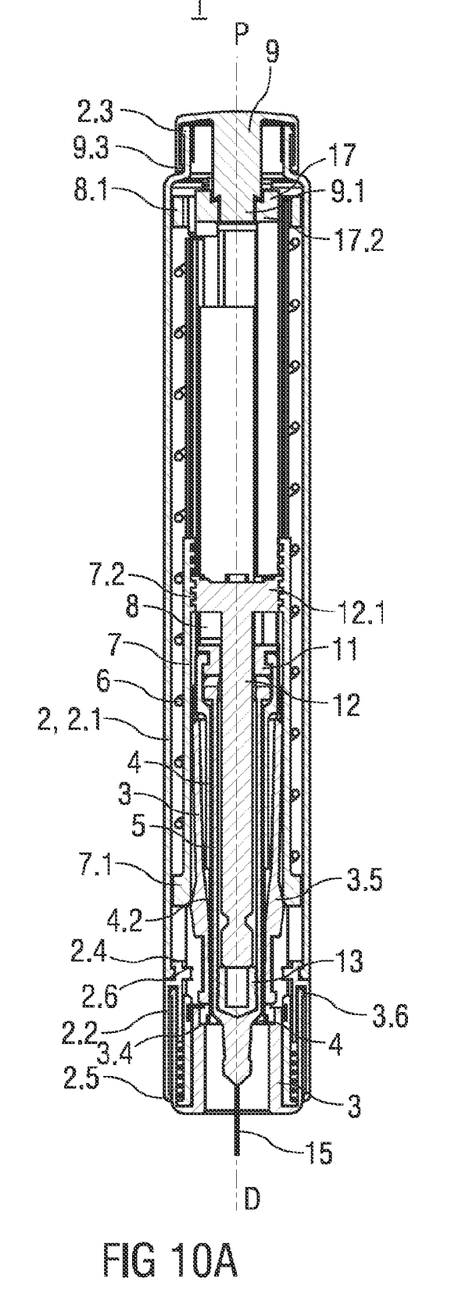
FIGS. 10A and 10B show two longitudinal sections of an exemplary embodiment of an autoinjector after an injection according to the present invention.
Figure 10B:
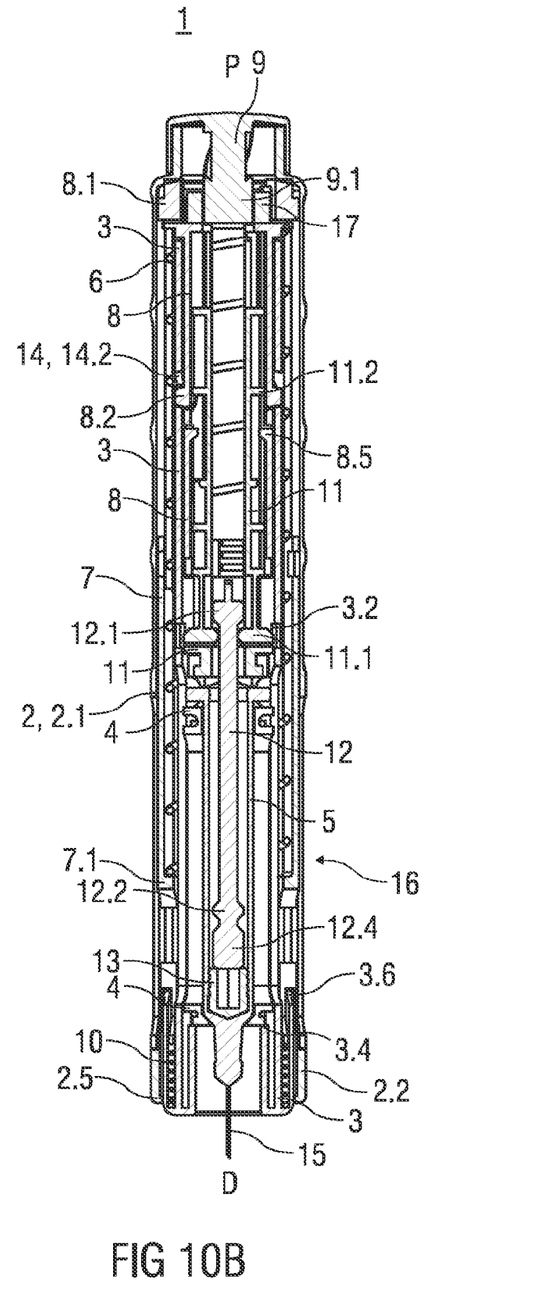

As shown in FIGS. 10A and 10B, when the front stop 4.1 on the syringe carrier 4 abuts the shroud shoulder 3.4 on the needle shroud 3, the resilient arms 11.1 of the coupling carrier 11 align with the first apertures 3.2 of the needle shroud 3, and the force of the drive spring 6 causes the first plunger shoulder 12.2 to deflect the resilient arms 11.1 of the coupling carrier 11 into the first apertures 3.2. When the resilient arms 11.1 are deflected, the inner plunger 12 moves in the distal direction D relative to the coupling carrier 11. The inner plunger 12 abuts a stopper 13 in the syringe 5 and pushes the stopper 13 in the distal direction D to expel the medicament from the needle 15.

As the outer plunger 7 translates in the distal direction D, the shoulders 7.1 engage the shroud latches 3.5, and cause the shroud latches 3.5 to deflect radially.

Figure 11A:
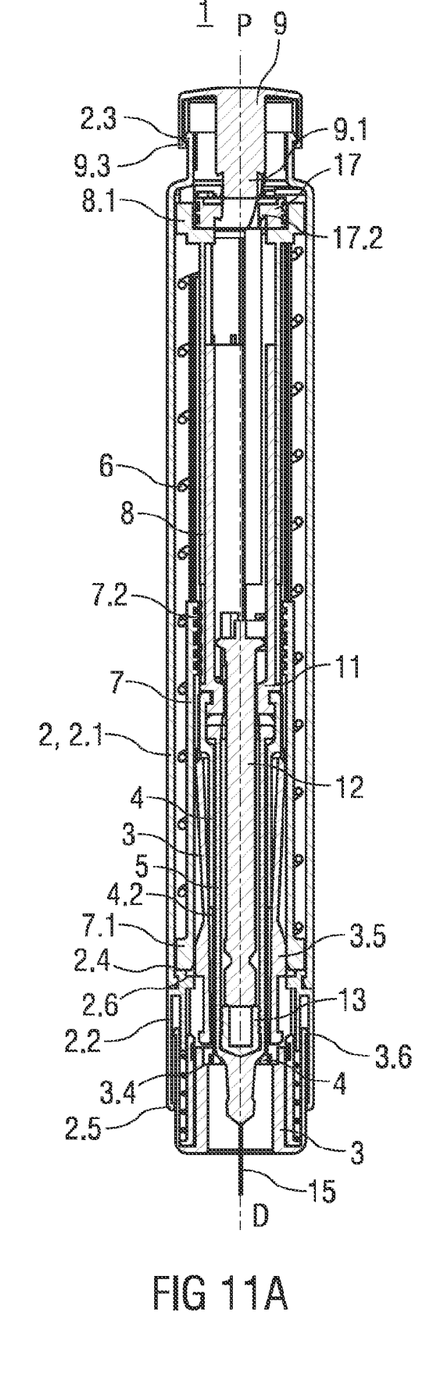
FIGS. 11A and 11B show two longitudinal sections of an exemplary embodiment of an autoinjector removed from an injection site according to the present invention.
Figure 11B:
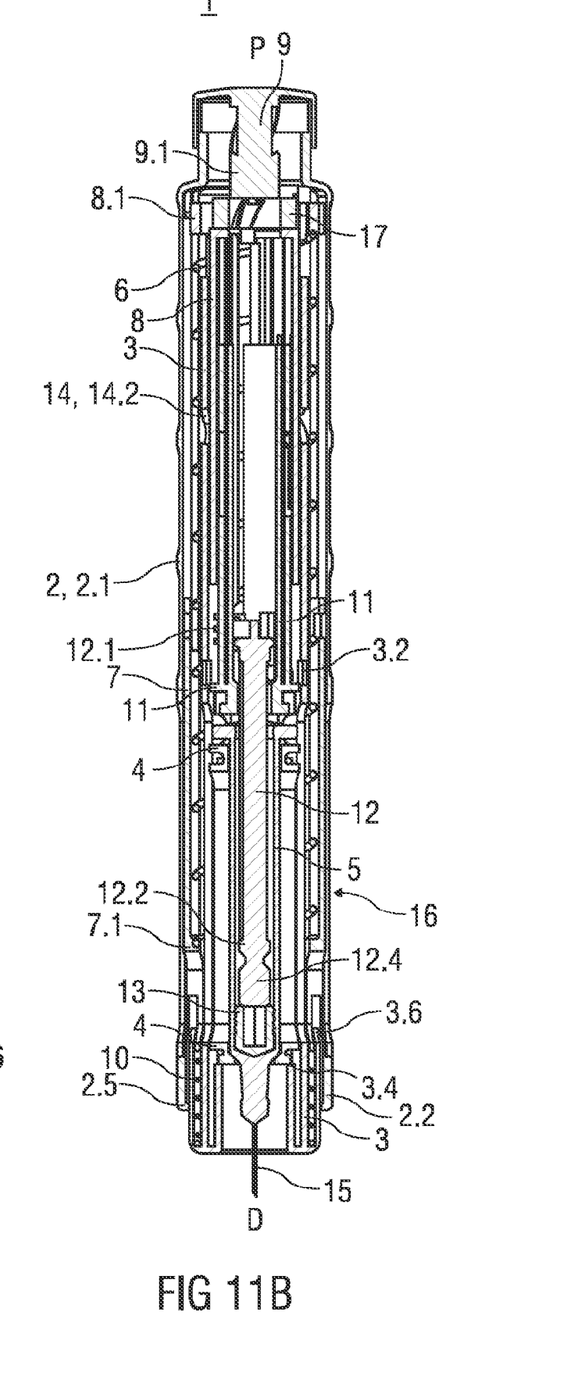

As shown in FIGS. 11A and 11B, when the autoinjector 1 is removed from the injection site after an injection is complete or during the injection, the biasing force of the control spring 10 causes the needle shroud 3 to translate in the distal direction D relative to the case 2. Under the force of the drive spring 6, the outer plunger 7 translates in the distal direction D relative to the case 2 until the shoulders 7.1 abut the distal case shoulder 2.4. In this position, the shroud latches 3.5 are deflected radially, and under the force of the control spring 10, the needle shroud 3 extends further beyond the distal end of the case 2, until hooks 3.6 on the needle shroud 3 engage the flange 2.5 on the distal end of the case 2 (as shown in FIGS. 11A and 11B).

As the needle shroud 3 translates in the distal direction D relative to the case 2, the engagement of the pin 8.2 on the chassis 8 and the guide track 14 causes the chassis 8 to rotate relative to the case 2. As the needle shroud 3 translates, the geometry of the guide track 14 causes the pin 8.2 to move through the angled portion 14.2 of the guide track 14 causing rotation of the chassis 8 relative to the needle shroud 3 and into the axial portion 14.1 of the guide track 14 which allows for axial movement of the needle shroud 3 relative to the chassis 8. Because the outer plunger 7 is keyed to the needle shroud 3, the chassis 8 rotates relative to the outer plunger 7 and causes rotation of the coupling carrier 11 which, in turn, rotates the inner plunger 12 to disengage from the outer plunger 7. Thus, the teeth 12.1 on the inner plunger 12 disengage the teeth 7.2 on the outer plunger 7. Further, extension of the needle shroud 3 relative to the case 2 is limited by the pin 8.2 abutting the proximal end of the axial portion 14.1 of the guide track 14 during translation of the needle shroud 3.

When the inner plunger 12 disengages the outer plunger 7, the force of the drive spring 6 does not act on the inner plunger 12. Thus, even if the autoinjector 1 is removed from the injection site during the injection, the expulsion of the medicament from the syringe 5 will stop, because there is no force to move the inner plunger 12 (and the stopper 13).

As the insertion depth of the needle 15 is defined by the syringe carrier 4 contacting the needle shroud 3, allowing the needle shroud 3 to re-advance on removal from the injection site could also allow the syringe 5 to advance further. In order to avoid this, one or more resilient clips 8.5 are arranged on the chassis 8 to engage a stop 11.2 on the coupling carrier 11 at the end of the rotation of the chassis 8. The clips 8.5 prevents the coupling carrier 11 (and the syringe carrier 4 coupled thereto and the syringe 5) from advancing in the distal direction D after the autoinjector 1 has been removed from the injection site.

Figure 13A:
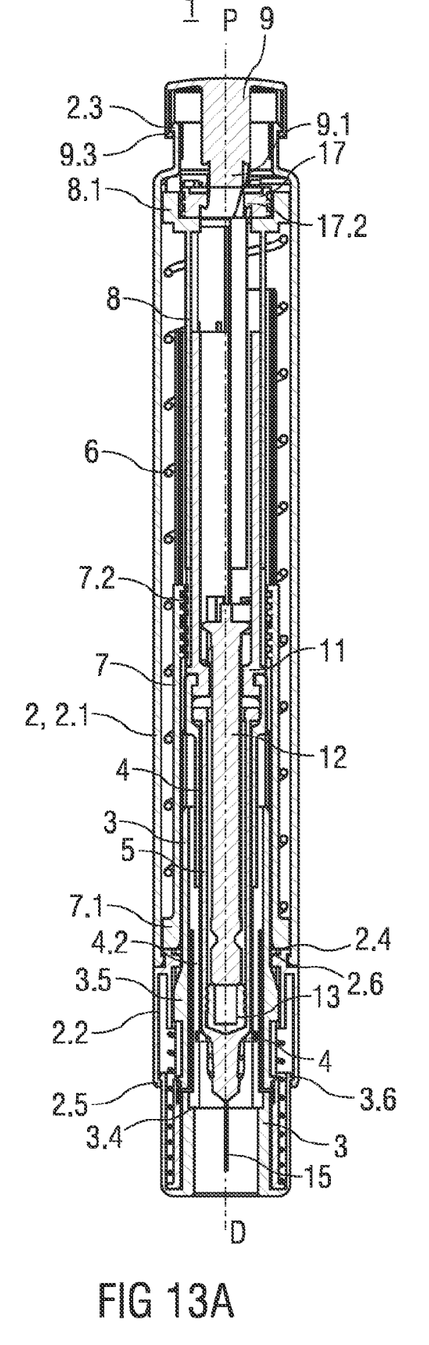
FIGS. 13A and 13B show two longitudinal sections of an exemplary embodiment of an autoinjector removed from an injection site according to the present invention.
Figure 13B:
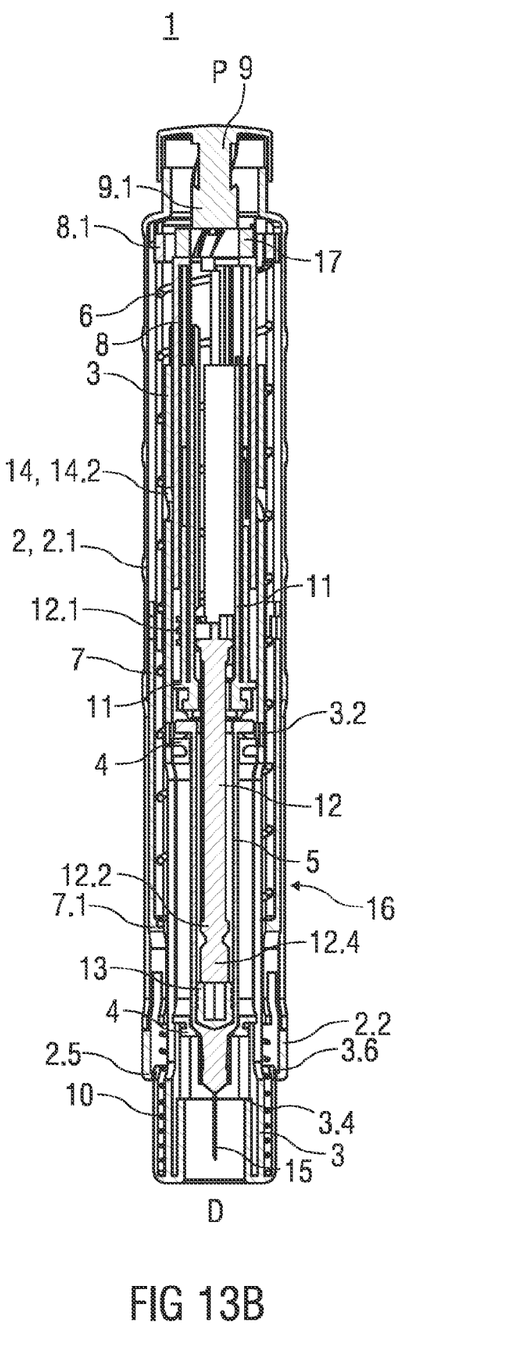

FIGS. 13A and 13B show the needle shroud 3 in its fully extended state. In an exemplary embodiment, a resilient non-return clip (not shown) may be arranged on the needle shroud 3 and adapted to engage the case 2 after the needle shroud 3 has been extended. The non-return clip may prevent the needle shroud 3 from moving in the proximal direction P relative to the case 2 if the autoinjector 1 is pressed against a subsequent injection site or during handling after an injection.

In an exemplary embodiment, a viewing window 16 is arranged in the case 2 for inspecting contents of the syringe 5.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(1ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

```
H-(Lys)4-des Pro36, des Pro37

Exendin-4(1-39)-NH2,

H-(Lys)5-des Pro36, des Pro37

Exendin-4(1-39)-NH2, des Pro36 Exendin-4(1-39), des Pro36 [Asp28]Exendin-4(1-39), des Pro36 [IsoAsp28]Exendin-4(1-39), des Pro36 [Met(O)14, Asp28]Exendin-4(1-39), des Pro36 [Met(O)14, IsoAsp28]Exendin-4(1-39), des Pro36 [Trp(O2)25, Asp28]Exendin-4(1-39), des Pro36 [Trp(O2)25, IsoAsp28]Exendin-4(1-39), des Pro36 [Met(O)14 Trp(O2)25, Asp28]

Exendin-4(1-39), des Pro36 [Met(O)14 Trp(O2)25, IsoAsp28]

Exendin-4(1-39);
or des Pro36 [Asp28]Exendin-4(1-39), des Pro36 [IsoAsp28]Exendin-4(1-39), des Pro36 [Met(O)14, Asp28]Exendin-4(1-39), des Pro36 [Met(O)14, IsoAsp28]Exendin-4(1-39), des Pro36 [Trp(O2)25, Asp28]Exendin-4(1-39), des Pro36 [Trp(O2)25, IsoAsp28]Exendin-4(1-39), des Pro36 [Met(O)14 Trp(O2)25, Asp28]

Exendin-4(1-39), des Pro36 [Met(O)14 Trp(O2)25, IsoAsp28]

Exendin-4(1-39),
``` wherein the group-Lys6-NH2 may be bound to the C-terminus of the Exendin-4 derivative;
or an Exendin-4 derivative of the sequence des Pro36 Exendin-4(1-39)-Lys6-NH2 (AVE0010), H-(Lys)6-des Pro36 [Asp28]Exendin-4(1-39)-Lys6-NH2, des Asp28 Pro36, Pro37, Pro38Exendin-4(1-39)-NH2, H-(Lys)6-des Pro36, Pro38 [Asp28]Exendin-4(1-39)-NH2, H-Asn-(Glu)5des Pro36, Pro37, Pro38 [Asp28]Exendin-4(1-39)-NH2, des Pro36, Pro37, Pro38 [Asp28]Exendin-4(1-39)-(Lys)6-NH2, H-(Lys)6-des Pro36, Pro37, Pro38 [Asp28]Exendin-4(1-39)-(Lys)6-NH2, H-Asn-(Glu)5-des Pro36, Pro37, Pro38 [Asp28]Exendin-4(1-39)-(Lys)6-NH2, H-(Lys)6-des Pro36 [Trp(O2)25, Asp28]Exendin-4(1-39)-Lys6-NH2, H-des Asp28 Pro36, Pro37, Pro38 [Trp(O2)25]Exendin-4(1-39)-NH2, H-(Lys)6-des Pro36, Pro37, Pro38 [Trp(O2)25, Asp28]Exendin-4(1-39)-NH2, H-Asn-(Glu)5-des Pro36, Pro37, Pro38 [Trp(O2)25, Asp28]Exendin-4(1-39)-NH2, des Pro36, Pro37, Pro38 [Trp(O2)25, Asp28]Exendin-4(1-39)-(Lys)6-NH2, H-(Lys)6-des Pro36, Pro37, Pro38 [Trp(O2)25, Asp28]Exendin-4(1-39)-(Lys)6-NH2, H-Asn-(Glu)5-des Pro36, Pro37, Pro38 [Trp(O2)25, Asp28]Exendin-4(1-39)-(Lys)6-NH2, H-(Lys)6-des Pro36 [Met(O)14, Asp28]Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28]Exendin-4(1-39)-NH2, H-Asn-(Glu)5-des Pro36, Pro37, Pro38 [Met(O)14, Asp28]Exendin-4(1-39)-NH2, des Pro36, Pro37, Pro38 [Met(O)14, Asp28]Exendin-4(1-39)-(Lys)6-NH2, H-(Lys)6-des Pro36, Pro37, Pro38 [Met(O)14, Asp28]Exendin-4(1-39)-(Lys)6-NH2, H-Asn-(Glu)5 des Pro36, Pro37, Pro38 [Met(O)14, Asp28]Exendin-4(1-39)-(Lys)6-NH2, H-Lys6-des Pro36 [Met(O)14, Trp(O2)25, Asp28]Exendin-4(1-39)-Lys6-NH2, H-des Asp28 Pro36, Pro37, Pro38 [Met(O)14, Trp(O2)25]Exendin-4(1-39)-NH2, H-(Lys)6-des Pro36, Pro37, Pro38 [Met(O)14, Asp28]Exendin-4(1-39)-NH2, H-Asn-(Glu)5-des Pro36, Pro37, Pro38 [Met(O)14, Trp(O2)25, Asp28]Exendin-4(1-39)-NH2, des Pro36, Pro37, Pro38 [Met(O)14, Trp(O2)25, Asp28]Exendin-4(1-39)-(Lys)6-NH2, H-(Lys)6-des Pro36, Pro37, Pro38 [Met(O)14, Trp(O2)25, Asp28]Exendin-4(S1-39)-(Lys)6-NH2, H-Asn-(Glu)5-des Pro36, Pro37, Pro38 [Met(O)14, Trp(O2)25, Asp28]Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
   a case;
   a needle shroud slidably arranged in the case;
   a chassis slidably arranged in the case, the chassis rotatably coupled to the needle shroud;
   an outer plunger selectively engaged to the chassis;
   an inner plunger selectively engaged to the outer plunger; and
   a drive spring applying a biasing force to the outer plunger, the biasing force being applied to the inner plunger when the inner plunger is engaged to the outer plunger,
   wherein axial movement of the needle shroud relative to the case causes rotation of the chassis relative to the needle shroud, and
   wherein the rotation of the chassis causes the inner plunger to rotate relative to the outer plunger and disengage the outer plunger to remove the biasing force from the drive spring on the inner plunger.

2. The autoinjector according to claim 1, further comprising:
   a firing nut rotatably disposed on the chassis, the firing nut engaging the outer plunger when in a first angular position and disengaging the outer plunger when in a second angular position.

3. The autoinjector according to claim 2, further comprising:
   a trigger button coupled to the case and selectively engaging the firing nut, wherein axial movement of the trigger button relative to the case causes rotation of the firing nut from the first angular position to the second angular position.

4. The autoinjector according to claim 2, wherein, when the firing nut is in the second angular position, the biasing force of the drive spring pushes the outer plunger in a distal direction relative to the case and pushes the chassis in a proximal direction relative to the case.

5. The autoinjector according to claim 1, wherein the needle shroud has a first axial position in which a first portion of the needle shroud extends beyond a distal end of the case, a second axial position in which the needle shroud is retracted into the case, and a third axial position in which a second portion of the needle shroud longer than the first portion extends beyond the distal end of the case.

6. The autoinjector according to claim 5, wherein, in the first axial position, resilient shroud latches on the needle shroud abut shoulders on the case.

7. The autoinjector according to claim 5, wherein the outer plunger engages the shroud latches which deflect and do not engage the shoulders on the case when the needle shroud translates from the second axial position to the third axial position.

8. The autoinjector according to claim 1, wherein the needle shroud includes a guide track adapted to engage a pin on the chassis.

9. The autoinjector according to claim 8, wherein the pin moves from an angled portion to an axial portion of the guide track causing rotation of the chassis relative to the needle shroud when the needle shroud translates from a second axial position to a third axial position.

10. The autoinjector according to claim 9, wherein the chassis includes a resilient clip adapted to engage a stop on a coupling carrier when the needle shroud is in the third axial position.

11. The autoinjector according to claim 1, further comprising:

a syringe carrier slidably disposed in the case, the syringe carrier adapted to hold a syringe.

12. The autoinjector according to claim 11, further comprising:

a coupling carrier coupled to the syringe carrier and selectively engaged to the inner plunger.

13. The autoinjector according to claim 12, wherein the coupling carrier includes resilient arms adapted to releasably engage the inner plunger, and wherein the biasing force of the drive spring causes the inner plunger to deflect the resilient arms when a front stop on the syringe carrier abuts a shroud shoulder on the needle shroud.

14. The autoinjector according to claim 13, wherein, when the resilient arms disengage the inner plunger, the inner plunger is adapted to push a stopper in the syringe.

15. The autoinjector according to claim 1, further comprising:

a control spring axially biasing the needle shroud relative to the case.

* * * * *

UNITED STATES PATENT AND TRADEMARK OFFICE
CERTIFICATE OF CORRECTION

PATENT NO. : 9,511,194 B2
APPLICATION NO. : 14/364242
DATED : December 6, 2016
INVENTOR(S) : Yannick Hourmand Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 198 days.

Signed and Sealed this
Tenth Day of April, 2018

Andrei Iancu
*Director of the United States Patent and Trademark Office*